US005254132A

United States Patent [19]
Barley et al.

[11] Patent Number: 5,254,132
[45] Date of Patent: Oct. 19, 1993

[54] METHODS FOR TREATING SUTURABLE WOUNDS BY USE OF SUTURES AND CYANOACRYLATE ADHESIVES

[75] Inventors: Linda M. Barley, Colorado Springs; J. Royce Renfrow, Mt. Crested Butte; Michael Byram, Colorado Springs, all of Colo.

[73] Assignee: MedLogic, Inc., Colorado Springs, Colo.

[21] Appl. No.: 938,838

[22] Filed: Sep. 1, 1992

[51] Int. Cl.$^5$ .............................................. A61B 17/00
[52] U.S. Cl. ................................................... 606/214
[58] Field of Search ................................. 606/213-215

[56] References Cited

U.S. PATENT DOCUMENTS

| | | |
|---|---|---|
| 2,804,073 | 8/1957 | Gallienne et al. |
| 3,527,224 | 9/1970 | Rabinowitz ......................... 606/214 |
| 3,559,652 | 2/1971 | Banitt ................................ 606/214 |
| 3,564,078 | 2/1971 | Wicker et al. ...................... 606/214 |
| 3,591,676 | 7/1971 | Hawkins et al. |
| 3,667,472 | 6/1972 | Halpern . |
| 3,759,264 | 9/1973 | Coover, Jr. et al. ................ 606/214 |
| 3,995,641 | 12/1976 | Kronenthal et al. |
| 4,035,334 | 7/1977 | Davydov et al. |
| 4,444,933 | 4/1984 | Columbus et al. .................. 524/292 |
| 4,650,826 | 3/1987 | Waniczek et al. .................. 524/730 |
| 4,958,748 | 9/1990 | Otake . |

OTHER PUBLICATIONS

Bhaskar, Surindar N. et al., "Healing of Skin Wounds with Butyl Cyanoacrylate", pp. 294-297, 1969, Journal of Dental Research, vol. 48, No. 2.

Dalvi, A. et al., "Non-suture Closure of Wound Using Cyanoacrylate", pp. 97-100, 1986, Journal of Postgraduate Medicine, vol. 32, No. 2.

Eiferman, Richard A. et al., "Antibacterial Effects of Cyanoacrylate Glue", pp. 958-960, Jun. 1983, Archives of Ophthalmology, vol. 101.

Ellis, David A. F. et al., "The Ideal Tissue Adhesive in Facial Plastic and Reconstructive Surgery", pp. 68-72, 1990, The Journal of Otolaryngology, vol. 19, No. 1.

Fung, Ramona Q. et al., "Use of Butyl-2-Cyanoacrylate in Rabbit Auricular Cartilage", pp. 459-464, Jul. 1985, Archives of Otolaryngology, vol. 111.

Galil, K. A. et al., "The Healing of Hamster Skin Ulcers Treated with N-butyl-2-cyanoacrylate (Histoacryl blue)", pp. 601-607, 1984, Journal of Biomedical Materials Research, vol. 18.

Harper, Marion C., "Stabilization of Osteochondral Fragments Using Limited Placement of Cyanoacrylate in Rabbits", pp. 272-276, Jun. 1988, Clinical Orthopaedics and Related Research 231.

Karner, Frank M. et al., "Histoacryl: Its Use in Aesthetic Facial Plastic Surgery", pp. 193-197, Feb. 1989, Archives of Otolaryngology Head and Neck Surgery, vol. 115.

Kosko, Paul I., "Upper Lid Blepharoplasty: Skin Closure Achieved with Butyl-2-Cyanoacrylate", pp. 424-425, Jun. 1981, Ophthalmic Surgery, vol. 12.

Lehman, Ralph A. W. et al., "Toxicity of Alkyl 2-Cyanoacrylate: Bacterial Growth", pp. 447-450, Sep. 1966, Archives of Surgery, vol. 93.

Leonard, Fred et al., "Synthesis and Degradation of Poly(alkyl-a-Cyanoacrylate)", pp. 259-272, 1966, Journal of Applied Polymer Science, vol. 10.

Makady, F. M. et al., "Effect of tissue adhesives and suture paterns on experimentally induced teat lacerations in lactating dairy cattle", pp. 1932-1934, Jun. 1991, JAVMA, Reports of Original Studies, vol. 198, No. 11.

Matsumoto, Teruo, "Bacteriology and Wound Healing", pp. 106-113, 1972, Chapter 3 in Tissue Adhesives in Surgery.

(List continued on next page.)

Primary Examiner—Stephen C. Pellegrino
Assistant Examiner—Gary Jackson
Attorney, Agent, or Firm—Burns, Doane, Swecker & Mathis

[57] ABSTRACT

Disclosed is a method for closing and covering suturable wounds under sterile conditions by using sutures or staples initially, in combination with cyanoacrylate adhesives as an adjunct covering and closure material.

8 Claims, No Drawings

OTHER PUBLICATIONS

Matsumoto, Teruo, "Clinical Considerations and Applications of Bucrylate Tissue Adhesive", pp. 226–237, 1972, Tissue Adhesives in Surgery, Chap. 1, Sec. III.

Matsumoto, Teruo, "Reactions of the Organism to Acrylate-Adhesives", pp. 436–444, 1972, Tissue Adhesives in Surgery.

Matsumoto, Teruo et al., "Tissue Adhesive and Wound Healing", pp. 266–271, Mar. 1969, Archives of Surgery, vol. 98.

Mizrahi, S. et al., "Use of Tissue Adhesives in the Repair of Lacerations in Children", pp. 312–313, Apr. 1988, Journal of Pediatric Surgery, vol. 23, No. 4.

Morton, R. J. et al., "The Use of Histoacryl Tissue Adhesive for the Primary Closure of Scalp Wounds", pp. 110–112, 1988, Archives of Emergency Medicine, vol. 5.

Ousterhout, D. K. et al., "Cutaneous Absorption of n-Alkyl-a-Cyanoacrylate", pp. 157–163, 1968, Journal of Biomedical Materials Research, vol. 2.

Pepper, D. C., "Kinetics and Mechanism of Zwitterionic Polymerization of Alkyl Cyanoacrylate", pp. 629–637, 1980, Polymer Journal, vol. 12, No. 9.

Pepper, David Charles et al., "Kinetics of Polymerization of Alkyl Cyanoacrylate by Tertiary Amines and Phosphines", pp. 395–410, 1983, Makromol. Chem., vol. 184.

Ronis, Max L. et al., "Review of Cyanoacrylate Tissue Glues with Emphasis of Their Otorhinolaryngological Applications", pp. 210–213, Feb. 1984, Laryngoscope., vol. 94.

Saches, Michael Evan., "Enbucrylate as Carilage Adhesive in Augmentation Rhinoplasty", pp. 389–393, Jun. 1985, Archives of Otolaryngology, vol. 111.

Toriumi, Dean M. et al., "Histotoxicity of Cyanoacrylate Tissue Adhesives: A Comparative Study", pp. 546–550, Jun. 1990, Archives of Otolaryngology Head and Neck Surgery, vol. 116.

Tseng, Yin-Chao et al., "Modification of Synthesis and Investigation of Properties for 2-cyanoacrylate", pp. 73–79, Jan. 1990, Biomaterials, vol. 11.

Vinters, H. V. et al., "The Histotoxicity of Cyanoacrylate: A Selective Review", pp. 279–291, 1985, Neuroradiology, vol. 27.

Watson, David P., "Use of Cyanoacrylate Tissue Adhesive for Closing Facial Lacerations in Children", p. 1014, Oct. 1989, British Medical Journal, vol. 299.

METHODS FOR TREATING SUTURABLE WOUNDS BY USE OF SUTURES AND CYANOACRYLATE ADHESIVES

BACKGROUND OF THE INVENTION

1. Field of the Invention

The present invention is directed to methods for closing and covering suturable wounds under sterile conditions by initially suturing or stapling the wound and afterwards, bonding the area adjacent to the sutures or staples with butyl-2-cyanoacrylate adhesives. The butyl-2-cyanoacrylate formulation to be used is typically stored in sterile dispensers for single use.

2. State of the Art

Cyanoacrylate adhesives have been suggested for a variety of adhesive purposes including glues and surgical adhesives. In particular, cyanoacrylate adhesives of formula I:

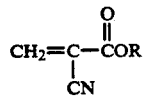
$$CH_2=C-COR \quad\quad I$$
with CN substituent wherein R is an alkyl or other suitable substituents are disclosed in U.S. Pat. Nos. 3,527,224; 3,591,676; 3,667,472; 3,995,641; 4,035,334; and 4,605,826. Typically, when used as adhesives for living tissues, the R substituent is alkyl of from 2 to 6 carbon atoms and most often is butyl (e.g., n-butyl).

The suggested medical uses for cyanoacrylate adhesives have been limited to surgical environments wherein the cyanoacrylate adhesives are utilized as an alternative to sutures and are employed in a sterile environment. See, for example, Halpern, U.S. Pat. No. 3,667,472. In surgical environments, the subcutaneous layers are typically joined together with sutures and the skin itself is joined either with sutures or with the cyanoacrylate adhesive. When the cyanoacrylate adhesive is employed, it is applied to separate sections of soft skin tissue under sterile conditions and the sections are then joined. Under these conditions, the cyanoacrylate adhesive bonds to the skin as well as polymerizes so as to join separate sections of soft tissue together.

The art discloses that when the cyanoacrylate adhesives successfully bind the skin, incidences of infection are reduced. However, the art also discloses that the use of cyanoacrylate adhesives as suture replacements can be accompanied by occasional adhesion failure resulting in wound reopening which requires closure by sutures. See, for example, Mizrahi, et al., "Use of Tissue Adhesives in the Repair of Lacerations in Children", *Journal of Pediatric Surgery*, Vol. 23, No. 4 (April), pp. 312–313 (1988). Fear of wound reopening apparently is one of the reasons surgeons have been reluctant to use any adhesives including cyanoacrylate based adhesives in place of sutures.

This invention is directed to methods for treating suturable wounds by first suturing or stapling the wound and then joining the skin between sutures or staples with a cyanoacrylate adhesive. When used in this manner, reductions in the rate of infection are contemplated.

In regard to the above, it is noted that while Morton, et al., Archives of Emergency Medicine, Vol. 5, pp. 110–112, (1988), discloses that butyl-2-cyanoacrylate adhesives can be used as a suture adjunct, the technique for surgical application is not specified. On the other hand, Makady, et al., JAVMA, Vol. 198, No. 11, June 1991, pp. 1932-1934, reports an experimental study using a combination of sutures and n-butyl-cyanoacrylate to close lacerations. This technique describes application of the cyanoacrylate over previously placed sutures in such a manner that the cyanoacrylate becomes entrapped deep in the wound. This technique resulted in inflammation, foreign body reaction, and ineffective healing.

SUMMARY OF THE INVENTION

The present invention is directed to specific methods for treating suturable wounds using sutures or staples and butyl-2-cyanoacrylate adhesive. The present invention overcomes the problems found with heretofore employed methods of using sutures with butyl-2-cyanoacrylate adhesive by first suturing or stapling the wound and then applying the adhesive onto the separated skin sections only between the sutures or staples to close and cover the area. When the sutures or staples are separated from each other by no more than 1.2 cm and no less than 0.6 cm, the incidence of wound opening will be reduced. Additionally, it is contemplated that when so used, the incidence of infection will also be reduced.

In view of the above, in one of its method aspects, this invention is directed to a method for closing the separated skin sections of a suturable wound which comprises the steps of:

(a) cleaning the wound;

(b) suturing or stapling the wound so that the sutures or staples are separated from each other by no more than about 1.2 centimeter and no less than about 0.6 centimeter;

(c) applying butyl-2-cyanoacrylate adhesive to the opposing separated skin sections between the sutures or staples in an amount sufficient so that upon polymerization, the skin sections are joined wherein the application is conducted so that contact of the cyanoacrylate adhesive with the sutures or staples is avoided; and (d) contacting the adjacent skin sections under conditions that permit the adhesive to polymerize so as to join separated skin sections.

In a preferred embodiment, the butyl-2-cyanoacrylate adhesive is n-butyl-2-cyanoacrylate and is applied at a rate of at least 0.02 milliliter (ml) of adhesive per square centimeter of skin which is to be covered.

In another preferred embodiment, the adhesive to be applied to the skin has a viscosity of from about 20 to about 100 centipoise at 20° C. More preferably, the adhesive is in monomeric form and has a viscosity of from about 20 to about 60 centipoise at 20° C.

As used herein, the following terms have the following meanings:

The term "butyl-2-cyanoacrylate adhesive" refers to adhesives based on monomers of formula I:

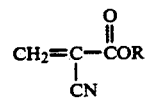
$$CH_2=C-COR \quad\quad I$$
with CN substituent where R is a butyl group, i.e., n-butyl, isobutyl, and the like. Preferably, R is n-butyl (i.e., $-CH_2CH_2CH_2CH_3$). These cyanoacrylate adhesives are known in the art and are described in, for example, U.S. Pat. Nos., 3,527,224; 3,551,676; 3,667,472; 3,995,641; 4,035,334; and 4,650,826 the disclosures of each are incorporated herein by reference in their entirety.

The butyl-2-cyanoacrylate adhesive rapidly polymerizes (thereby causing binding) in the presence of water vapor or tissue protein and is capable of bonding human tissue without causing histoxicity or cytotoxicity.

The term "suturable wounds" means wounds which are closed with sutures or staples whether used alone or in combination with butyl-2-cyanoacrylate adhesives. Typically, these wounds are of sufficient severity that non-suturable techniques to close the wound and stop bleeding are not applicable nor advised.

DETAILED DESCRIPTION OF THE PREFERRED EMBODIMENTS

The present invention relates to the treatment of suturable wounds by using a combination of sutures or staples and butyl-2-cyanoacrylate adhesive. When used in the specific methods of this invention, this combination effectively closes the wound while providing reduced incidences of infection.

The butyl-2-cyanoacrylate adhesive used in combination with sutures or staples can be monomeric or partially polymeric. In general, partially polymerized butyl-2-cyanoacrylate adhesives are liquid polymers having a higher viscosity than that of the corresponding monomer and, therefore, are better suited for those applications which are intended to be specific for a particular skin area. In other words, less viscous materials are more likely to "run" (i.e., flow) into areas where application was not intended.

The butyl-2-cyanoacrylate adhesives used herein preferably have a viscosity of from about 20 to about 100 centipoise and more preferably from about 20 to about 60 centipoise at 20° C. The specific viscosity of the formulation depends on the amount and degree of partially polymerized butyl-2-cyanoacrylate adhesive employed. Such factors are readily ascertainable by the skilled artisan. For example, methods for preparing partially polymerized butyl-2-cyanoacrylate adhesives are disclosed, for example, by Rabinowitz, U.S. Pat. No. 3,527,224 which is incorporated herein by reference in its entirety.

Upon application of the adhesive to the separated skin sections, the sections are coupled and contact with skin moisture and tissue protein is sufficient to polymerize the butyl-2-cyanoacrylate adhesive or, in the case of partially polymerized butyl-2-cyanoacrylate adhesives, to further polymerize, at ambient conditions (skin temperature) over 10 seconds to 60 seconds resulting in the joining of the separated skin sections.

The adhesive is applied in an amount sufficient so that upon polymerization, the separated skin sections are joined without diffusing into the tissue in amounts to cause irritation or necrosis. Typically, the adhesive is applied at a rate of at least about 0.02 ml of cyanoacrylate adhesive per square centimeter of skin. In this regard, application of the butyl-2-cyanoacrylate adhesive to the sutures or staples should be avoided because the adhesive can penetrate into the skin punctures formed by the sutures or staples thereby resulting in inflammation and delayed healing. In any event, the butyl-2-cyanoacrylate adhesive results in an airtight, waterproof bonding of the separated skin sections which does not need to be replaced when the wound gets wet and forms a covering and barrier to external contaminants. Once applied, the bonding of the separated skin sections minimizes bacterial and contaminant entry into the wound, thus, reducing the rate of secondary infection. Generally, the adhesive coating does not limit dexterity and promotes faster wound healing. Additional benefits include reduced scarring and potentially less patient discomfort during the healing process.

FORMULATIONS

The cyanoacrylate adhesive formulations employed herein generally comprise monomeric and/or partially polymerized compounds of butyl-2-cyanoacrylate. These compositions are liquid in nature and, upon contact with skin moisture and proteins, will polymerize so as to permit separated skin sections to be fused.

The formulations may additionally contain one or more optional additives such as colorants, perfumes, anti-diffusion agents, modifying agents antibiotics, and stabilizers. In practice, each of these optional additives should be both miscible and compatible with the butyl-2-cyanoacrylate adhesive. Compatible additives are those that do not prevent the use of the cyanoacrylate adhesives for their intended use.

In general, colorants are added so that the polymerized film will contain a discrete and discernable color thereby permitting their accurate application to the desired positions. Perfumes are added to provide a pleasant smell to the formulation. Stabilizers are added to minimize in situ polymerization in containers during storage. Each of these additives are conventional. For example, suitable stabilizers are disclosed in U.S. Pat. No. 4,650,826 the disclosure of which is incorporated herein by reference in its entirety.

The formulation is generally stored in a sterile applicator for use in a single dose application. Single dose applicators include those having breakable or removable seals that prevent moisture, including atmospheric moisture, from contacting the formulation an causing in situ polymerization and are preferably adaptable for use with a syringe. When used with a syringe, the syringe is also stored under sterile conditions.

METHODOLOGY

In the methods described herein, the suturable wounds are initially cleaned with any suitable disinfectant well known in the art and then closed. If necessary, the separated subcutaneous portions of the wound are joined together by conventional suturing techniques prior to closing. The opposing separated skin sections are then joined by first suturing the wounds with conventional sutures (e.g., staples, polyamide nonabsorbable vertical mattress sutures, and the like). The sutures are applied using conventional techniques. However, it is necessary that suturing procedure be controlled so that the distance separating individual sutures is not less than 0.6 centimeters or greater than 1.2 centimeters. Specifically, when the distance between sutures is greater than 1.2 centimeters, problems can be encountered with maintaining wound closure between sutures. Contrarily, when the distance between sutures is about 0.5 centimeters or less, the distance is so small that it becomes increasingly difficult to prevent application of the butyl-2-cyanoacrylate adhesive to the separated skin areas between sutures without intrusion of the adhesive into the puncture wounds formed by the sutures.

In a second step, after the wound is sutured, the separated skin sections between sutures or between the terminus of the wound and the first suture adjacent thereto are joined by application of butyl-2-cyanoacrylate adhesive to either or both of the separated opposing skin edges which are then brought together under conditions sufficient to permit the adhesive to polymerize and thereby joining the separated skin sections. In this regard, care is taken during application of the adhesive to either or both of the opposing skin sections so as to avoid application of the adhesive onto the suture. In this regard, if the adhesive is applied to the suture, the adhesive can penetrate into the puncture wound formed during suturing resulting in inflammation, foreign body reaction, and ineffective healing.

In general, sufficient butyl-2-cyanoacrylate adhesive is employed so that upon polymerization the separated opposing skin sections are effectively joined. Typically, the adhesive is applied at a rate of at least about 0.02 milliliter of cyanoacrylate adhesive per square centimeter of skin surface area and preferably from about 0.02 milliliter to about 0.05 milliliter of cyanoacrylate adhesive.

The amount of cyanoacrylate adhesive applied onto the skin surface area is typically controlled by use of a sterile syringe, sterile applicator, or other similar dispensing devices. The syringe preferably has suitable dimensions to permit the controlled dispensing of the adhesive onto the skin.

Upon application of the butyl-2-cyanoacrylate adhesive, the opposing separated sections of skin are brought into contact with one another by conventional means (e.g., forceps), and the surface skin moisture, tissue protein, and temperature are sufficient to initiate polymerization of the adhesive upon application. Thereafter, the skin surface is maintained under suitable conditions to allow polymerization to proceed to complete the joining of the separated skin sections.

In general, the particular length of time required for polymerization will vary depending on factors such as the amount of adhesive applied, the temperature of the skin, the moisture content of the skin, the surface area of the wound and the like. However, in a preferred embodiment, polymerization is generally complete in about 10 seconds to about 60 seconds while the skin is maintained at ambient conditions. During this period, the opposing skin sections are merely maintained together by, for example, a forceps. After the polymerization is complete, the opposing skin sections strongly adhere to each other while the bond between these skin sections is flexible and waterproof thereby protecting the wound area and promoting healing.

In general, the polymer will adhere to the skin for a period of about 3 to 7 days after which time it sloughs off. By this time, the healing process is sufficiently complete that there is little danger of wound reopening.

The following example illustrates certain embodiments of the invention but is not meant to limit the scope of the claims in any way.

EXAMPLE

A cyanoacrylate adhesive formulation is prepared in monomeric form using n-butyl-2-cyanoacrylate. The formulation is placed into a sterile syringe for use during closing of a suturable wound.

In this example, a typical suturable human wound is treated as follows. After the wound is cleaned with a suitable disinfectant and, if necessary, the separated subcutaneous sections coupled by suturing, the surface of the wound is closed by first suturing the wound by placing staples about 0.9 centimeters apart along the length of the wound. N-butyl-2-cyanoacrylate adhesive having a viscosity of about 30 to 60 centipoise at 20° C. is then syringed onto the opposing separated skin sections between the sutures at a rate of about 0.05 ml per square centimeter. Care is taken to ensure that the adhesive is not applied onto the staples. The opposing skin sections are then contacted with each other by a forceps and maintained in this position under otherwise ambient conditions (temperature, humidity, etc.) for about 30 seconds. At this time, polymerization is complete and the separated opposing skin areas are joined to each other. The forceps are then removed. If any of the adhesive has contacted the forceps so as to prevent forceps removal, acetone can be used to dissolve the polymer adhering to the instrument.

From the foregoing description, various modifications and changes in the composition and method will occur to those skilled in the art. All such modifications coming within the scope of the appended claims are intended to be included therein.

What is claimed is:

1. A method for closing the separated skin sections of a suturable wound which comprises the steps of:
   (a) cleaning the wound;
   (b) suturing or stapling the separated skin sections of the wound so that the sutures or staples are separated from each other by no more than about 1.2 centimeters and no less than about 0.6 centimeter;
   (c) applying butyl-2-cyanoacrylate adhesive to the opposing and still separated skin sections between the sutures or staples in an amount sufficient so that upon polymerization, the skin sections are joined wherein the application is conducted so that contact of the cyanoacrylate adhesive with the sutures or staples is avoided; and
   (d) contacting the adjacent separated skin sections under conditions that permit the adhesive to polymerize so as to join separated skin sections.

2. A method according to claim 1 wherein said adhesive is applied to said wound in an amount of at least 0.02 ml of butyl-2-cyanoacrylate adhesive per square centimeter of skin which is to be joined.

3. A method according to claim 1 wherein the butyl-2-cyanoacrylate adhesive has a viscosity of from about 20 to about 100 centipoise at 20° C.

4. The method according to claim 3 wherein the butyl-2-cyanoacrylate adhesive has a viscosity of from about 20 to about 60 centipoise at 20° C.

5. The method according to claim 1 wherein the butyl-2-cyanoacrylate adhesive is applied at a concentration of from about 0.02 ml to about 0.05 ml per square centimeter.

6. The method according to claim 1 wherein the butyl-2-cyanoacrylate adhesive is n-butyl-2-cyanoacrylate adhesive.

7. The method according to claim 1 wherein said application of butyl-2-cyanoacrylate adhesive to the opposing separated skin sections between the sutures or staples is achieved with a sterile syringe.

8. The method according to claim 1 which, prior to step (b), further comprises the steps of joining separated subcutaneous portions of the wound together by sutures.

* * * * *